(12) United States Patent
Spiegal et al.

(10) Patent No.: US 8,323,184 B2
(45) Date of Patent: Dec. 4, 2012

(54) SURGICAL ACCESS PORT AND ASSOCIATED INTRODUCER MECHANISM

(75) Inventors: Heidi Spiegal, Hamden, CT (US); Gregory G. Okoniewski, North Haven, CT (US); David A. Rezac, Westborough, MA (US)

(73) Assignee: Covidien LP, Mansfield, MA (US)

( * ) Notice: Subject to any disclaimer, the term of this patent is extended or adjusted under 35 U.S.C. 154(b) by 211 days.

(21) Appl. No.: 12/719,085

(22) Filed: Mar. 8, 2010

(65) Prior Publication Data

US 2010/0249523 A1    Sep. 30, 2010

Related U.S. Application Data

(60) Provisional application No. 61/164,971, filed on Mar. 31, 2009.

(51) Int. Cl.
*A61B 1/32* (2006.01)
(52) U.S. Cl. .......................................... 600/206; 600/215
(58) Field of Classification Search .......... 600/201–246; 623/1.11, 1.12, 1.23, 2.11
See application file for complete search history.

(56) References Cited

U.S. PATENT DOCUMENTS

| | | |
|---|---|---|
| 4,016,884 A | 4/1977 | Kwan-Gett |
| 4,112,932 A | 9/1978 | Chiulli |
| 4,183,357 A | 1/1980 | Bentley et al. |
| 4,402,683 A | 9/1983 | Kopman |
| 4,653,476 A | 3/1987 | Bonnet |
| 4,863,430 A | 9/1989 | Klyce et al. |
| 4,863,438 A | 9/1989 | Gauderer et al. |
| 5,073,169 A | 12/1991 | Raiken |
| 5,082,005 A | 1/1992 | Kaldany |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,242,409 A | 9/1993 | Buelna |
| 5,242,415 A | 9/1993 | Kantrowitz et al. |
| 5,257,973 A | 11/1993 | Villasuso |

(Continued)

FOREIGN PATENT DOCUMENTS

EP    0807416    11/1997

(Continued)

OTHER PUBLICATIONS

European Search Report EP 10250638.3 dated Aug. 5, 2010.
European Search Report for corresponding EP 10 25 1317 dated Oct. 25, 2010.
International Search Report EP 10 25 0643 dated Jul. 5, 2010.

*Primary Examiner* — Alvin Stewart
*Assistant Examiner* — Lynnsy Schneider

(57) ABSTRACT

A surgical portal assembly includes a portal member adapted for positioning within a tissue tract and defining a longitudinal axis with leading and trailing ends. The portal member includes at least one longitudinal port for passage of an object. The portal member comprises a compressible material adapted to transition between a first expanded condition to facilitate securing of the portal within the tissue tract and in substantial sealed relation with tissue surfaces defining the tissue tract, and a second compressed condition to facilitate at least partial insertion of the portal within the tissue tract. The portal assembly also includes an elongated member extending through the at least one longitudinal port and mechanically couplable to the portal member adjacent the leading end thereof. The elongated member is adapted to move through the at least one longitudinal port in a trailing direction to exert a compressive force at least adjacent the leading end to cause the portal member to transition toward the compressed condition.

8 Claims, 6 Drawing Sheets

U.S. PATENT DOCUMENTS

| | | | |
|---|---|---|---|
| 5,257,975 A | 11/1993 | Foshee | |
| 5,269,772 A | 12/1993 | Wilk | |
| 5,312,391 A | 5/1994 | Wilk | |
| 5,330,486 A | 7/1994 | Wilk | |
| 5,334,143 A | 8/1994 | Carroll | |
| 5,345,927 A | 9/1994 | Bonutti | |
| 5,366,478 A | 11/1994 | Brinkerhoff et al. | |
| 5,375,588 A | 12/1994 | Yoon | |
| 5,391,156 A | 2/1995 | Hildwein et al. | |
| 5,395,367 A | 3/1995 | Wilk | |
| 5,437,683 A | 8/1995 | Neumann et al. | |
| 5,460,170 A | 10/1995 | Hammerslag | |
| 5,480,410 A | 1/1996 | Cuschieri et al. | |
| 5,490,843 A | 2/1996 | Hildwein et al. | |
| 5,507,758 A | 4/1996 | Thomason et al. | |
| 5,511,564 A | 4/1996 | Wilk | |
| 5,514,133 A | 5/1996 | Golub et al. | |
| 5,514,153 A | 5/1996 | Bonutti | |
| 5,522,791 A | 6/1996 | Leyva | |
| 5,524,644 A | 6/1996 | Crook | |
| 5,540,648 A | 7/1996 | Yoon | |
| 5,545,179 A | 8/1996 | Williamson, IV | |
| 5,577,993 A | 11/1996 | Zhu et al. | |
| 5,601,581 A | 2/1997 | Fogarty et al. | |
| 5,634,911 A | 6/1997 | Hermann et al. | |
| 5,634,937 A | 6/1997 | Mollenauer et al. | |
| 5,649,550 A | 7/1997 | Crook | |
| 5,651,771 A | 7/1997 | Tangherlini et al. | |
| 5,653,705 A | 8/1997 | de la Torre et al. | |
| 5,672,168 A | 9/1997 | de la Torre et al. | |
| 5,683,378 A | 11/1997 | Christy | |
| 5,685,857 A | 11/1997 | Negus et al. | |
| 5,713,858 A | 2/1998 | Heruth et al. | |
| 5,713,869 A | 2/1998 | Morejon | |
| 5,728,103 A | 3/1998 | Picha et al. | |
| 5,730,748 A | 3/1998 | Fogarty et al. | |
| 5,735,791 A | 4/1998 | Alexander, Jr. et al. | |
| 5,741,298 A | 4/1998 | MacLeod | |
| 5,782,817 A | 7/1998 | Franzel et al. | |
| 5,795,290 A | 8/1998 | Bridges | |
| 5,803,921 A | 9/1998 | Bonadio | |
| 5,810,712 A | 9/1998 | Dunn | |
| 5,813,409 A | 9/1998 | Leahy et al. | |
| 5,830,191 A | 11/1998 | Hildwein et al. | |
| 5,836,871 A | 11/1998 | Wallace et al. | |
| 5,842,971 A | 12/1998 | Yoon | |
| 5,848,992 A | 12/1998 | Hart et al. | |
| 5,853,417 A | 12/1998 | Fogarty et al. | |
| 5,857,461 A | 1/1999 | Levitsky et al. | |
| 5,865,817 A | 2/1999 | Moenning et al. | |
| 5,871,474 A | 2/1999 | Hermann et al. | |
| 5,876,413 A | 3/1999 | Fogarty et al. | |
| 5,894,843 A | 4/1999 | Benetti et al. | |
| 5,899,208 A | 5/1999 | Bonadio | |
| 5,899,913 A | 5/1999 | Fogarty et al. | |
| 5,904,703 A | 5/1999 | Gilson | |
| 5,906,577 A | 5/1999 | Beane et al. | |
| 5,916,198 A | 6/1999 | Dillow | |
| 5,941,898 A | 8/1999 | Moenning et al. | |
| 5,951,588 A | 9/1999 | Moenning | |
| 5,957,913 A | 9/1999 | de la Torre et al. | |
| 5,964,781 A | 10/1999 | Mollenauer et al. | |
| 5,976,174 A | 11/1999 | Ruiz | |
| 5,997,515 A | 12/1999 | de la Torre et al. | |
| 6,017,355 A | 1/2000 | Hessel et al. | |
| 6,018,094 A | 1/2000 | Fox | |
| 6,024,736 A | 2/2000 | de la Torre et al. | |
| 6,033,426 A | 3/2000 | Kaji | |
| 6,033,428 A | 3/2000 | Sardella | |
| 6,042,573 A | 3/2000 | Lucey | |
| 6,048,309 A | 4/2000 | Flom et al. | |
| 6,059,816 A | 5/2000 | Moenning | |
| 6,068,639 A | 5/2000 | Fogarty et al. | |
| 6,077,288 A | 6/2000 | Shimomura et al. | |
| 6,086,603 A | 7/2000 | Termin et al. | |
| 6,099,506 A | 8/2000 | Macoviak et al. | |
| 6,110,154 A | 8/2000 | Shimomura et al. | |
| 6,142,936 A | 11/2000 | Beane et al. | |
| 6,171,282 B1 | 1/2001 | Ragsdale | |
| 6,197,002 B1 | 3/2001 | Peterson | |
| 6,217,555 B1 | 4/2001 | Hart et al. | |
| 6,228,063 B1 * | 5/2001 | Aboul-Hosn | 604/174 |
| 6,238,373 B1 | 5/2001 | de la Torre et al. | |
| 6,241,768 B1 | 6/2001 | Agarwal et al. | |
| 6,254,534 B1 | 7/2001 | Butler et al. | |
| 6,264,604 B1 | 7/2001 | Kieturakis et al. | |
| 6,315,770 B1 | 11/2001 | de la Torre et al. | |
| 6,319,246 B1 | 11/2001 | de la Torre et al. | |
| 6,371,968 B1 * | 4/2002 | Kogasaka et al. | 606/190 |
| 6,382,211 B1 | 5/2002 | Crook | |
| 6,423,036 B1 | 7/2002 | Van Huizen | |
| 6,440,061 B1 | 8/2002 | Wenner et al. | |
| 6,440,063 B1 | 8/2002 | Beane et al. | |
| 6,443,957 B1 | 9/2002 | Addis | |
| 6,447,489 B1 | 9/2002 | Peterson | |
| 6,450,983 B1 | 9/2002 | Rambo | |
| 6,454,783 B1 | 9/2002 | Piskun | |
| 6,464,686 B1 | 10/2002 | O'Hara et al. | |
| 6,468,292 B1 | 10/2002 | Mollenauer et al. | |
| 6,488,620 B1 | 12/2002 | Segermark et al. | |
| 6,488,692 B1 | 12/2002 | Spence et al. | |
| 6,527,787 B1 | 3/2003 | Fogarty et al. | |
| 6,551,270 B1 * | 4/2003 | Bimbo et al. | 604/93.01 |
| 6,558,371 B2 | 5/2003 | Dorn | |
| 6,578,577 B2 | 6/2003 | Bonadio et al. | |
| 6,582,364 B2 | 6/2003 | Butler et al. | |
| 6,589,167 B1 | 7/2003 | Shimomura et al. | |
| 6,613,952 B2 | 9/2003 | Rambo | |
| 6,623,426 B2 | 9/2003 | Bonadio et al. | |
| 6,669,674 B1 | 12/2003 | Macoviak et al. | |
| 6,676,639 B1 | 1/2004 | Ternström | |
| 6,706,050 B1 | 3/2004 | Giannadakis | |
| 6,723,044 B2 | 4/2004 | Pulford et al. | |
| 6,723,088 B2 | 4/2004 | Gaskill, III et al. | |
| 6,725,080 B2 | 4/2004 | Melkent et al. | |
| 6,800,084 B2 | 10/2004 | Davison et al. | |
| 6,811,546 B1 | 11/2004 | Callas et al. | |
| 6,814,078 B2 | 11/2004 | Crook | |
| 6,837,893 B2 | 1/2005 | Miller | |
| 6,840,946 B2 | 1/2005 | Fogarty et al. | |
| 6,840,951 B2 | 1/2005 | de la Torre et al. | |
| 6,846,287 B2 | 1/2005 | Bonadio et al. | |
| 6,863,674 B2 | 3/2005 | Kasahara et al. | |
| 6,878,110 B2 | 4/2005 | Yang et al. | |
| 6,890,295 B2 | 5/2005 | Michels et al. | |
| 6,913,609 B2 | 7/2005 | Yencho et al. | |
| 6,916,310 B2 | 7/2005 | Sommerich | |
| 6,916,331 B2 | 7/2005 | Mollenauer et al. | |
| 6,929,637 B2 | 8/2005 | Gonzalez et al. | |
| 6,939,296 B2 * | 9/2005 | Ewers et al. | 600/206 |
| 6,945,932 B1 | 9/2005 | Caldwell et al. | |
| 6,958,037 B2 | 10/2005 | Ewers et al. | |
| 6,972,026 B1 | 12/2005 | Caldwell et al. | |
| 6,991,602 B2 | 1/2006 | Nakazawa et al. | |
| 6,997,909 B2 | 2/2006 | Goldberg | |
| 7,001,397 B2 | 2/2006 | Davison et al. | |
| 7,008,377 B2 | 3/2006 | Beane et al. | |
| 7,014,628 B2 | 3/2006 | Bousquet | |
| 7,033,319 B2 | 4/2006 | Pulford et al. | |
| 7,052,454 B2 | 5/2006 | Taylor | |
| 7,056,321 B2 | 6/2006 | Pagliuca et al. | |
| 7,077,852 B2 | 7/2006 | Fogarty et al. | |
| 7,081,089 B2 | 7/2006 | Bonadio et al. | |
| 7,083,626 B2 | 8/2006 | Hart et al. | |
| 7,100,614 B2 | 9/2006 | Stevens et al. | |
| 7,101,353 B2 | 9/2006 | Lui et al. | |
| 7,153,261 B2 | 12/2006 | Wenchell | |
| 7,163,510 B2 | 1/2007 | Kahle et al. | |
| 7,192,436 B2 | 3/2007 | Sing et al. | |
| 7,195,590 B2 | 3/2007 | Butler et al. | |
| 7,214,185 B1 | 5/2007 | Rosney et al. | |
| 7,217,277 B2 | 5/2007 | Parihar et al. | |
| 7,223,257 B2 | 5/2007 | Shubayev et al. | |
| 7,223,278 B2 | 5/2007 | Davison et al. | |
| 7,235,084 B2 | 6/2007 | Skakoon et al. | |
| 7,238,154 B2 | 7/2007 | Ewers et al. | |
| 7,276,075 B1 | 10/2007 | Callas et al. | |

| | | | | | | |
|---|---|---|---|---|---|---|
| 7,294,103 B2 | 11/2007 | Bertolero et al. | | 2007/0093695 A1 | 4/2007 | Bonadio et al. |
| 7,300,399 B2 | 11/2007 | Bonadio et al. | | 2007/0118175 A1 | 5/2007 | Butler et al. |
| 7,316,699 B2 | 1/2008 | McFarlane | | 2007/0149859 A1 | 6/2007 | Albrecht et al. |
| 7,331,940 B2 | 2/2008 | Sommerich | | 2007/0151566 A1 | 7/2007 | Kahle et al. |
| 7,344,547 B2 | 3/2008 | Piskun | | 2007/0156023 A1 | 7/2007 | Frasier et al. |
| 7,377,898 B2 | 5/2008 | Ewers et al. | | 2007/0185387 A1 | 8/2007 | Albrecht et al. |
| 7,393,322 B2 | 7/2008 | Wenchell | | 2007/0203398 A1 | 8/2007 | Bonadio et al. |
| 7,412,977 B2 | 8/2008 | Fields et al. | | 2007/0208312 A1 | 9/2007 | Norton et al. |
| 7,445,597 B2 | 11/2008 | Butler et al. | | 2007/0225569 A1 | 9/2007 | Ewers et al. |
| 7,473,221 B2 | 1/2009 | Ewers et al. | | 2007/0270654 A1 | 11/2007 | Pignato et al. |
| 7,481,765 B2 | 1/2009 | Ewers et al. | | 2007/0270882 A1 | 11/2007 | Hjelle et al. |
| 7,537,564 B2 | 5/2009 | Bonadio et al. | | 2008/0027476 A1 | 1/2008 | Piskun |
| 7,540,839 B2 | 6/2009 | Butler et al. | | 2008/0048011 A1 | 2/2008 | Weller |
| 7,559,893 B2 | 7/2009 | Bonadio et al. | | 2008/0091143 A1 | 4/2008 | Taylor et al. |
| 7,645,232 B2 | 1/2010 | Shluzas | | 2008/0097162 A1 | 4/2008 | Bonadio et al. |
| 7,650,887 B2 | 1/2010 | Nguyen et al. | | 2008/0161826 A1 | 7/2008 | Guiraudon |
| 7,704,207 B2 | 4/2010 | Albrecht et al. | | 2008/0200767 A1 | 8/2008 | Ewers et al. |
| 7,717,847 B2 | 5/2010 | Smith | | 2008/0255519 A1 | 10/2008 | Piskun et al. |
| 7,727,146 B2 | 6/2010 | Albrecht et al. | | 2008/0319261 A1 | 12/2008 | Lucini |
| 7,736,306 B2 | 6/2010 | Brustad et al. | | 2009/0012477 A1 | 1/2009 | Norton et al. |
| 7,766,824 B2 | 8/2010 | Jensen et al. | | 2009/0093752 A1 | 4/2009 | Richard et al. |
| 7,798,898 B2 | 9/2010 | Luciano, Jr. et al. | | 2009/0093850 A1 | 4/2009 | Richard |
| 7,811,251 B2 | 10/2010 | Wenchell et al. | | 2009/0131751 A1 | 5/2009 | Spivey et al. |
| 7,815,567 B2 | 10/2010 | Albrecht et al. | | 2009/0137879 A1 | 5/2009 | Ewers et al. |
| 7,837,612 B2 | 11/2010 | Gill et al. | | 2009/0182279 A1 | 7/2009 | Wenchell et al. |
| 7,896,889 B2 | 3/2011 | Mazzocchi et al. | | 2009/0187079 A1 | 7/2009 | Albrecht et al. |
| 7,909,760 B2 | 3/2011 | Albrecht et al. | | 2009/0221968 A1 | 9/2009 | Morrison et al. |
| 2001/0037053 A1 | 11/2001 | Bonadio et al. | | 2009/0227843 A1 | 9/2009 | Smith et al. |
| 2002/0038077 A1 | 3/2002 | de la Torre et al. | | 2009/0326330 A1 | 12/2009 | Bonadio et al. |
| 2002/0183594 A1 | 12/2002 | Beane et al. | | 2009/0326332 A1 | 12/2009 | Carter |
| 2003/0014076 A1 | 1/2003 | Mollenauer et al. | | 2009/0326461 A1 | 12/2009 | Gresham |
| 2003/0105473 A1 | 6/2003 | Miller | | 2010/0063452 A1 | 3/2010 | Edelman et al. |
| 2003/0135091 A1 | 7/2003 | Nakazawa et al. | | 2010/0100043 A1 | 4/2010 | Racenet |
| 2003/0236549 A1 | 12/2003 | Bonadio et al. | | 2010/0240960 A1 | 9/2010 | Richard |
| 2004/0015185 A1 | 1/2004 | Ewers et al. | | 2010/0249516 A1 | 9/2010 | Shelton, IV et al. |
| 2004/0049099 A1 | 3/2004 | Ewers et al. | | 2010/0312061 A1 | 12/2010 | Hess et al. |
| 2004/0049100 A1 | 3/2004 | Butler et al. | | | | |
| 2004/0073090 A1 | 4/2004 | Butler et al. | | FOREIGN PATENT DOCUMENTS | | |
| 2004/0092795 A1 | 5/2004 | Bonadio et al. | | EP | 0950376 | 10/1999 |
| 2004/0092796 A1 | 5/2004 | Butler et al. | | EP | 1312318 | 5/2003 |
| 2004/0111061 A1 | 6/2004 | Curran | | EP | 1312318 B1 | 12/2005 |
| 2004/0138529 A1 | 7/2004 | Wiltshire et al. | | EP | 1 774 918 A1 | 4/2007 |
| 2004/0167543 A1 | 8/2004 | Mazzocchi et al. | | EP | 2044889 A1 | 4/2009 |
| 2004/0267096 A1 | 12/2004 | Caldwell et al. | | EP | 2044897 | 4/2009 |
| 2005/0020884 A1 | 1/2005 | Hart et al. | | EP | 2098182 | 9/2009 |
| 2005/0043592 A1 | 2/2005 | Boyd et al. | | EP | 2 181 657 | 5/2010 |
| 2005/0090716 A1 | 4/2005 | Bonadio et al. | | EP | 2181657 | 5/2010 |
| 2005/0090717 A1 | 4/2005 | Bonadio et al. | | EP | 2 289 438 | 3/2011 |
| 2005/0096695 A1 | 5/2005 | Olich | | WO | WO93/14801 | 8/1993 |
| 2005/0148823 A1 | 7/2005 | Vaugh et al. | | WO | WO 93/14801 | 8/1993 |
| 2005/0192483 A1 | 9/2005 | Bonadio et al. | | WO | WO 94/04067 | 3/1994 |
| 2005/0203346 A1 | 9/2005 | Bonadio et al. | | WO | WO96/36283 | 11/1996 |
| 2005/0240082 A1 | 10/2005 | Bonadio et al. | | WO | WO 97/33520 | 9/1997 |
| 2005/0241647 A1 | 11/2005 | Nguyen et al. | | WO | WO97/42889 | 11/1997 |
| 2005/0267419 A1 | 12/2005 | Smith | | WO | WO 97/42889 | 11/1997 |
| 2005/0288558 A1 | 12/2005 | Ewers et al. | | WO | WO 99/16368 | 4/1999 |
| 2006/0020241 A1 | 1/2006 | Piskun et al. | | WO | WO99/22804 | 5/1999 |
| 2006/0030755 A1 | 2/2006 | Ewers et al. | | WO | WO00/32116 | 6/2000 |
| 2006/0071432 A1 | 4/2006 | Staudner | | WO | WO00/32120 | 6/2000 |
| 2006/0084842 A1 | 4/2006 | Hart et al. | | WO | WO01/08581 | 2/2001 |
| 2006/0129165 A1 | 6/2006 | Edoga et al. | | WO | WO01/32116 | 5/2001 |
| 2006/0149137 A1 | 7/2006 | Pingleton et al. | | WO | WO 01/49363 A1 | 7/2001 |
| 2006/0149306 A1 | 7/2006 | Hart et al. | | WO | WO 02/07611 A2 | 1/2002 |
| 2006/0161049 A1 | 7/2006 | Beane et al. | | WO | WO03/034908 | 5/2003 |
| 2006/0161050 A1 | 7/2006 | Butler et al. | | WO | WO03/071926 | 9/2003 |
| 2006/0241651 A1 | 10/2006 | Wilk | | WO | WO2004/043275 | 5/2004 |
| 2006/0247498 A1 | 11/2006 | Bonadio et al. | | WO | WO2004/054456 | 7/2004 |
| 2006/0247499 A1 | 11/2006 | Butler et al. | | WO | WO2004/075741 | 9/2004 |
| 2006/0247500 A1 | 11/2006 | Voegele et al. | | WO | WO2004/075930 | 9/2004 |
| 2006/0247516 A1 | 11/2006 | Hess et al. | | WO | WO2006/019723 | 2/2006 |
| 2006/0247586 A1 | 11/2006 | Voegele et al. | | WO | WO2006/100658 | 9/2006 |
| 2006/0247673 A1 | 11/2006 | Voegele et al. | | WO | WO 2006/100658 A2 | 9/2006 |
| 2006/0247678 A1 | 11/2006 | Weisenburgh, II et al. | | WO | WO2006/110733 | 10/2006 |
| 2006/0258899 A1 | 11/2006 | Gill et al. | | WO | WO 2006/115893 | 11/2006 |
| 2006/0270911 A1 | 11/2006 | Voegele et al. | | WO | WO 2008/011358 | 1/2008 |
| 2007/0088202 A1 | 4/2007 | Albrecht et al. | | WO | WO2008/015566 | 2/2008 |
| 2007/0088204 A1 | 4/2007 | Albrecht et al. | | | | |
| 2007/0088241 A1 | 4/2007 | Brustad et al. | | | | |
| 2007/0088258 A1 | 4/2007 | Wenchell et al. | | | | |

| WO | WO 2008/015566 A2 | 2/2008 |
| WO | WO2008/042005 | 4/2008 |
| WO | WO 2008/093313 A1 | 8/2008 |
| WO | WO2008/103151 | 8/2008 |
| WO | WO2008/121294 | 10/2008 |
| WO | WO 2008/121294 A1 | 10/2008 |
| WO | WO2009/036343 | 3/2009 |

* cited by examiner

SURGICAL ACCESS PORT AND ASSOCIATED INTRODUCER MECHANISM

CROSS REFERENCE TO RELATED APPLICATION

The present application claims the benefit of and priority to U.S. Provisional Application Ser. No. 61/164,971 filed on Mar. 31, 2009, the entire contents of which are incorporated herein by reference.

BACKGROUND

1. Technical Field

The present disclosure relates generally to ports for use in minimally invasive surgical procedures, such as endoscopic and/or laparoscopic procedures, and more particularly, relates to an access port and an associated introducer mechanism to assist in deploying the port within a tissue tract of a patient.

2. Description of Related Art

Minimally invasive surgery is a type of surgery performed through one or more small incisions in a patient's body, usually less than an inch in dimension. Some advantages of minimal invasive surgery is that patients have less trauma to the body, lose less blood, have smaller surgical scars, and need less pain medication.

During a typical minimally invasive procedure, surgical objects, such as surgical access devices, e.g., trocar and cannula assemblies, or endoscopes, are inserted into the patient's body through the incision in tissue. In general, prior to the introduction of the surgical object into the patient's body, insufflation gasses are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various ports with valves and seals are used during the course of minimally invasive procedures and are widely known in the art. However, a continuing need exists for an access pot and associated introducer mechanism which can position the access port with relative ease and with minor inconvenience for the surgeon.

SUMMARY

Accordingly, in accordance with one embodiment of the present disclosure, a surgical portal assembly includes a portal member adapted for positioning within a tissue tract and defining a longitudinal axis with leading and trailing ends. The portal member includes at least one longitudinal port for passage of an object. The portal member comprises a compressible material adapted to transition between a first expanded condition to facilitate securing of the portal within the tissue tract and in substantial sealed relation with tissue surfaces defining the tissue tract, and a second compressed condition to facilitate at least partial insertion of the portal within the tissue tract. An elongated member extends through the at least one longitudinal port and is mechanically couplable to the portal member adjacent the leading end thereof. The elongated member is adapted to move through the at least one longitudinal port in a trailing direction to exert a compressive force at least adjacent the leading end to cause the portal member to transition toward the compressed condition. The portal member may include first and second longitudinal ports having respective first and second elongated members extending therethrough and being attachable to the portal member adjacent the leading end thereof. The first and second elongated members are adapted to move through the respective first and second longitudinal ports in the trailing direction to cause the portal member to transition toward the compressed condition. The portal may include a third longitudinal port with a third elongated member extending therethrough and being attachable to the portal member adjacent the leading end thereof. The third elongated member is adapted to move through the third longitudinal port in the trailing direction to cause the portal member to transition toward the compressed condition.

Other embodiments and a method of use of the portal assembly are also envisioned.

BRIEF DESCRIPTION OF THE DRAWINGS

The above and other aspects, features, and advantages of the present disclosure will become more apparent in light of the following detailed description when taken in conjunction with the accompanying drawings in which:

FIG. 1A is a perspective view of an surgical portal assembly in accordance with the principles of the present disclosure illustrating the portal member and the elongated constraining members extending through the portal member;

FIG. 1B is a longitudinal cross-sectional view of the surgical portal assembly of FIG. 1A illustrating the portal member in a first expanded condition;

FIG. 3A is a perspective view of another embodiment of the surgical portal assembly in accordance with another embodiment of the present disclosure illustrating the portal member in a normal expanded condition;

FIG. 3B is a perspective view of the surgical portal assembly of FIG. 3B with at least the leading end of the portal member in a compressed condition;

DETAILED DESCRIPTION

Figure 1C:
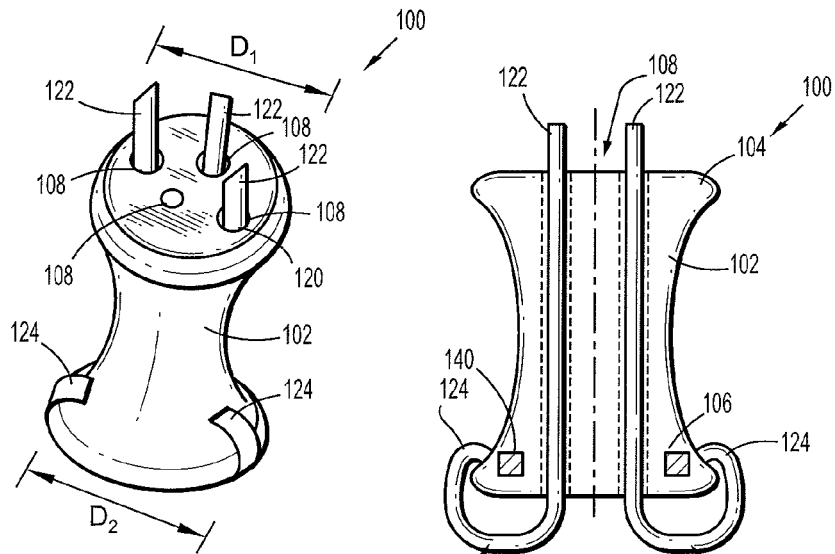
FIG. 1C is a longitudinal cross-sectional view of the surgical portal assembly of FIGS. 1A and 1B illustrating the portal member in a second compressed condition and being inserted within a tissue tract of a patient.
Figure 1C:
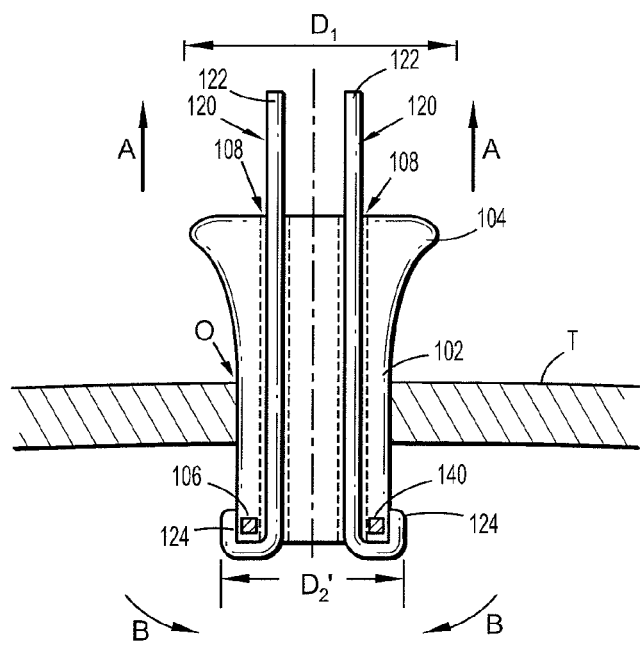

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is further from the user. In the following description, well-known functions or constructions are not described in detail to avoid obscuring the present disclosure in unnecessary detail.

One type of minimal invasive surgery described herein is referred to as a single-incision laparoscopic surgery (SILS). SILS is an advanced minimally invasive surgical procedure which would permit a surgeon to operate through a single entry point, typically the patient's navel. The disclosed SILS procedure involves insufflating the body cavity and positioning a port within, e.g., the navel of the patient. Instruments including an endoscope and additional instruments such as graspers, staplers, forceps or the like may be introduced within the port to carry out the surgical procedure.

The port assembly in the SILS procedure may be introduced into an incision with a Kelly clamp. However, the Kelly clamp may limit the surgeon's ability to properly place a SILS port due to the limited length of the Kelly clamp's arm and handle. Furthermore, visibility may become an issue due to the presence of the clamp and the surgeon's hand holding the clamp. Removal of the Kelly clamp subsequent to placement of the port may also present undesired obstacles.

Referring now to the drawings, in which like reference numerals identify identical or substantially similar parts throughout the several views, FIGS. 1A and 1B illustrate a port assembly 100 in accordance with the principles of the present disclosure. Port assembly 100 includes a portal member 102 having including at least one longitudinal port 108, possibly, a plurality of longitudinal ports 108 extending along the axis "k" of the portal member 102. One or more elongated constraining members 120 extend through the longitudinal ports 108. At least one or more inner longitudinal ports 108 are dimensioned to receive a surgical object (not shown) therethrough. The portal member 102 has a proximal trailing end 104 having a first dimension D1 and a distal leading end 106 having a second dimension D2 when the portal member 102 is in a normal expanded condition. The portal member 102 may be made from a disposable, compressible, and/or flexible type material, for example, but not limited to, a suitable foam or gel material having sufficient compliance to form a seal about one or more surgical objects, shown generally as surgical object, and also establish a sealing relation with the tissue. The foam is preferably sufficiently compliant to accommodate off axis motion of the surgical object. In one embodiment, the foam includes a polyisoprene material. Suitable portal members are disclosed in commonly assigned U.S. patent application Ser. No. 12/244,024, filed Oct. 2, 2008, the entire contents of which is hereby incorporated by reference herein.

Each elongated member 120 has a first end 122 and a second end 124. Elongated member 124 spans the length of the portal member 102. The first end 122 of the elongated member 120 is positioned at the proximal trailing end 104 of the portal member 102, while the second end 124 of the elongated member 120 is attached to the distal leading end 106 of the portal member 102. The elongated member 120 may be attached to the distal leading end 106 of the portal member 102 by any suitable attaching technique, such as for example, gluing, stapling and suturing. Further, the elongated member 120 may be made from any suitable material, for example, but not limited to, plastic, metal, and shape-memory alloy.

Turning now to FIG. 1C, the second dimension D2 defined by distal leading end 106 is configured to decrease, to a shorter diameter or length D2'. This occurs when the first end 122 of each elongated member 120 is pulled in a proximal trailing direction, depicted by directional arrow A, by a clinician, thereby also pulling second end 124. In this manner, the distal leading end 106 is pulled towards the center of the portal member 102, which movement is depicted by a directional arrow B, since the second end 124 of the elongated member 120 is attached to the distal leading end 106.

FIG. 1A illustrates, in an exemplary embodiment, the surgical portal assembly 102 having three (3) elongated members passed through each respective longitudinal port 108. However, one skilled in the art will appreciate that any number of elongated members and longitudinal ports may be used and implemented with the surgical portal assembly 100. Thus, the surgical portal assembly 100 may further include one or more outer longitudinal ports 108 that are defined within the portal member 102 and are configured to contain one or more elongated members 120. As discussed above, the elongated member may be coupled to an outer portion of the distal leading end 124 of the portal member 102. Any means for coupling elongated member 120 to portal member 102 are envisioned including cements, adhesives, welding or the like. It is also envisioned that elongated member 120 may be releasably connected to portal member 102 whereby pulling on the elongated member 120 to exert a force which exceeds a predetermine value will cause release of the elongated member 120 from the portal member 102. Instruments may be introduced within longitudinal ports 108 when the elongated members 120 are removed. As a further alternative, an instrument may be positioned within a longitudinal port 108 in the presence of an elongated member 120. The compressive material of fabrication of portal member 102 will ensure that a seal is established and maintained about the instrument.

Portal member 102 may include a substantially annular ring 140 of spring material, such as stainless steel or a shape memory material. Annular ring 140 may deform or compress when distal leading end 206 of portal member 202 is compressed, and returns to its normal annular shape upon release of the first end 122 of elongated member 120, thus biasing distal leading end 106 to its normal state of FIG. 1B. Annular ring 140 may be embedded within or attached to portal member 102 during manufacture.

In accordance with the present disclosure, a method of introducing a surgical portal assembly is provided. Referring back to FIGS. 1A-1C, in an initial step of the method, a surgical portal assembly, as described above, is provided to a surgical site. In a next step, the first end 122 of each elongated member 120 is pulled in a proximal trailing direction, as depicted by directional arrow A, such that the second dimension D2 of the distal leading end 106 compresses and decreases to a smaller dimension D2'. Thereafter, the surgical portal assembly 100 is deployed into a tissue tract T of a patient, which has been previously prepared by a clinician. In a following step, the first end 122 of the elongated member 120 is released by a user such that the smaller second dimension D2' of the distal leading end 106 increases to a larger second dimension D2, i.e., the portal member returns to its normal expanded condition with distal leading end 106 expanding to substantially secure the surgical portal assembly 100 at a desired surgical location within a tissue tract T. The presence of annular ring 140 may facilitate this transformation as discussed hereinabove.

Figure 2A:
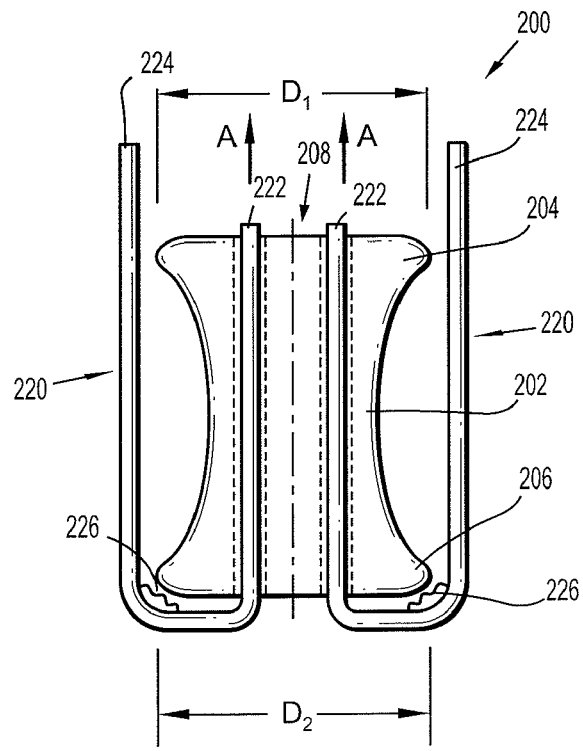
FIG. 2A is a longitudinal cross-sectional view of a surgical portal assembly in accordance with another embodiment of the present disclosure illustrating the portal member in a first expanded condition.
Figure 2B:
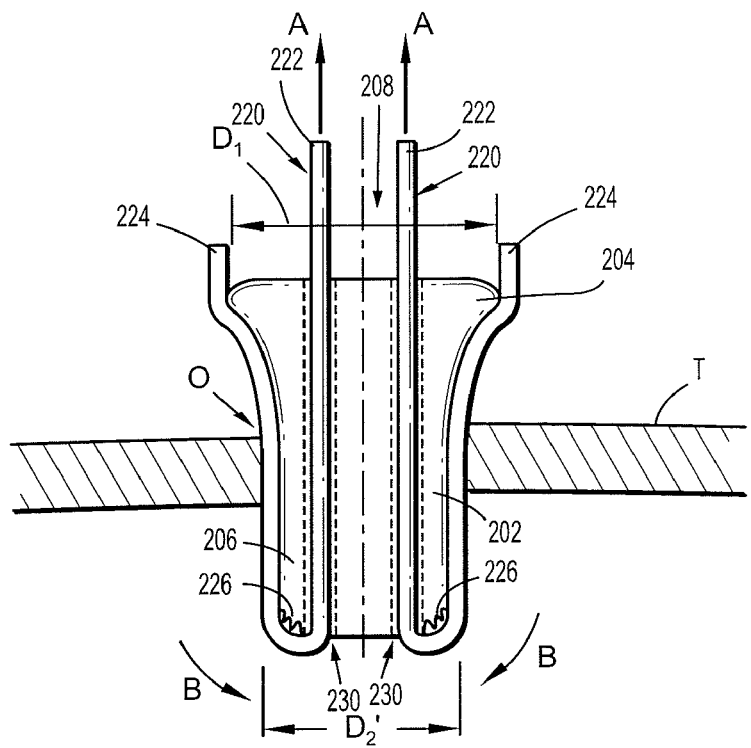
FIG. 2B is a longitudinal cross-sectional view of the surgical portal assembly of FIG. 2A showing the surgical portal assembly being deployed within a tissue tract of a patient illustrating the portal member in a second compressed condition and being inserted within a tissue tract of a patient.
Figure 2C:
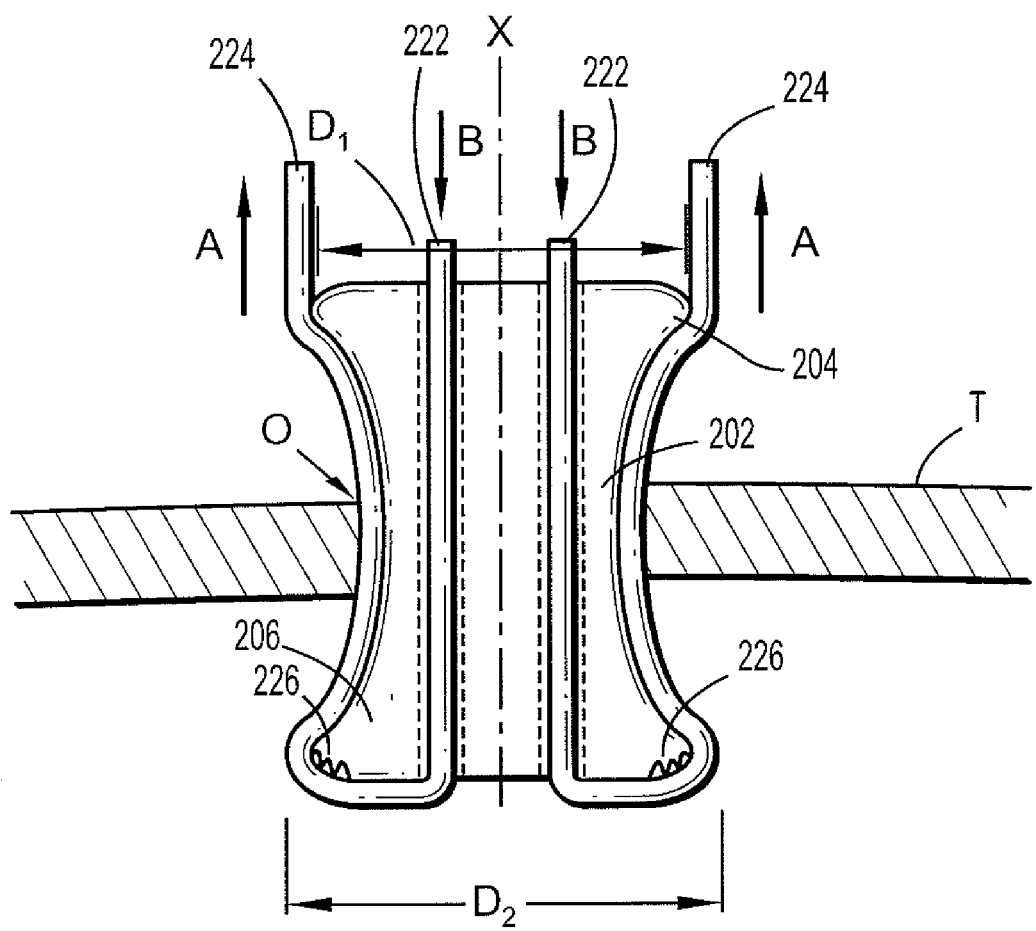
FIG. 2C is a longitudinal cross-sectional view of the surgical portal assembly of FIGS. 2A and 2B illustrating the portal member deployed within a tissue tract.

In another exemplary embodiment, shown in FIGS. 2A-2C, one or more elongated members may continuously run along the length of an outer surface of the portal member 202 and back up through a respective longitudinal ports 230 of the portal member. In this configuration, each first and second ends 222, 224 of respective elongated members 220 is adjacent to proximal trailing end 204 of a portal member 202.

In disclosed embodiments, each elongated member 220 may have an irregular surface or grip portion 226 that may mechanically couple to a distal leading end 206 of the portal member 202. For example, the grip portion 226 of the elongated member 220 may contain a barbed texture, a hook and loop fastener, or any suitable irregularly surfaced material.

To introduce the portal member within the incision, e.g., in the navel, the first or inner end 222 of each elongated member 220 is pulled in a proximal trailing direction, depicted by directional arrow A, such that the second dimension D2 of the distal leading end 206 decreases to smaller dimension D2'. The surgical portal assembly is inserted into a tissue tract T of a patient. Thereafter, the second end 224 of each elongated member 220 is pulled in a proximal trailing direction, depicted by directional arrow A, such that the second smaller dimension D2' of the distal leading end 206 increases to a second larger dimension D2, thus the distal leading end 206 of the surgical portal assembly 200 is substantially secured in the tissue tract T of the patient. Instruments may be introduced within central passage 208 or any of the longitudinal ports 230 to perform the desired procedure. In this embodiment, portal member 202 may also comprises a malleable material such that distal leading end 206 returns to its normal uncompressed condition in response to movement of second ends 224. Such malleable materials are inclusive of metals which may be embedded within the resilient compressible foam. In the alternative, portal member 202 be composed entirely of the malleable material.

Figure 3C:
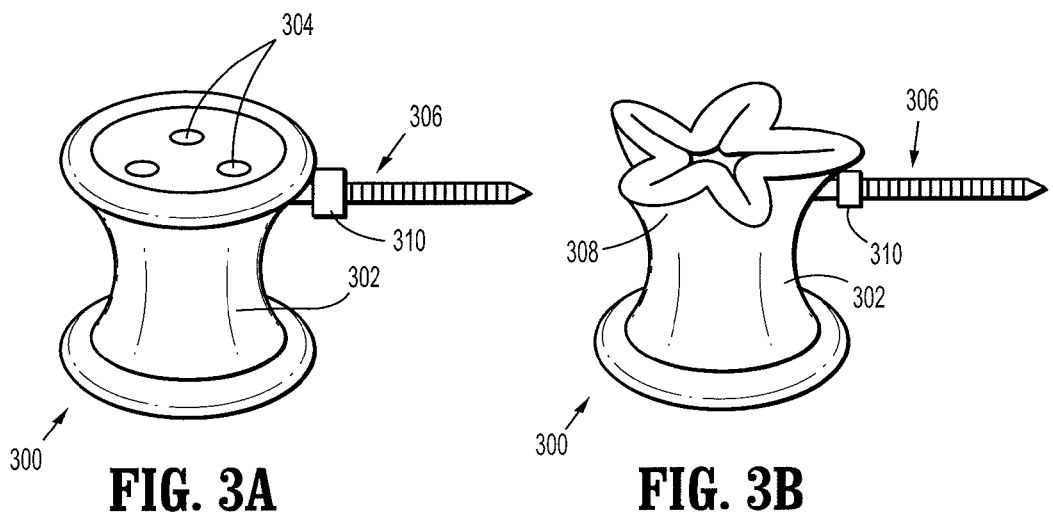
FIG. 3C is a longitudinal cross-sectional view of the surgical portal assembly of FIG. 3A.
Figure 3C:
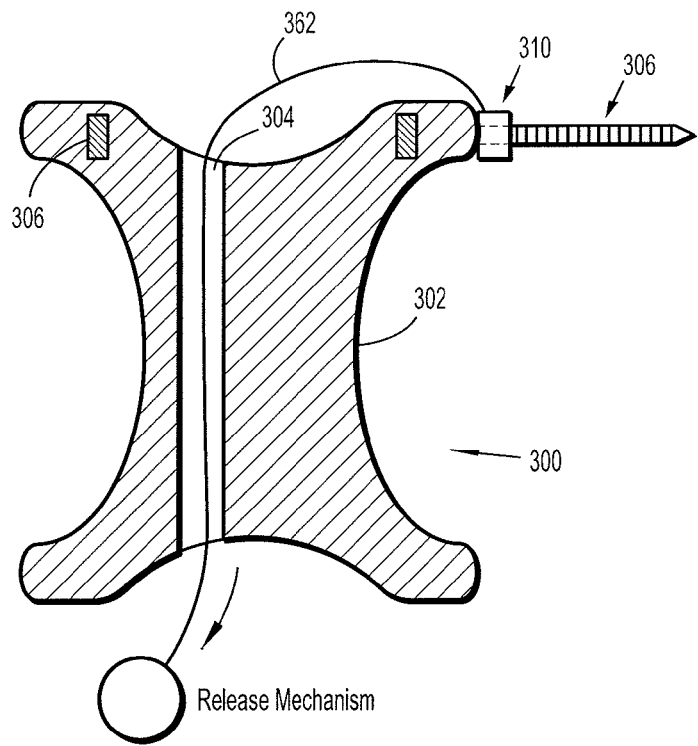
Figure 4A:
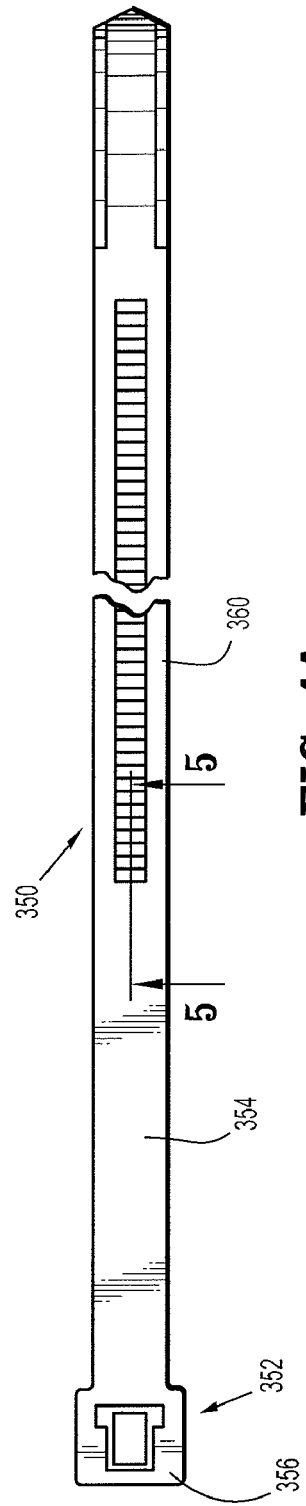
FIGS. 4A-4B are views of the constraining member of the surgical portal assembly of FIG. 3A.
Figure 4B:
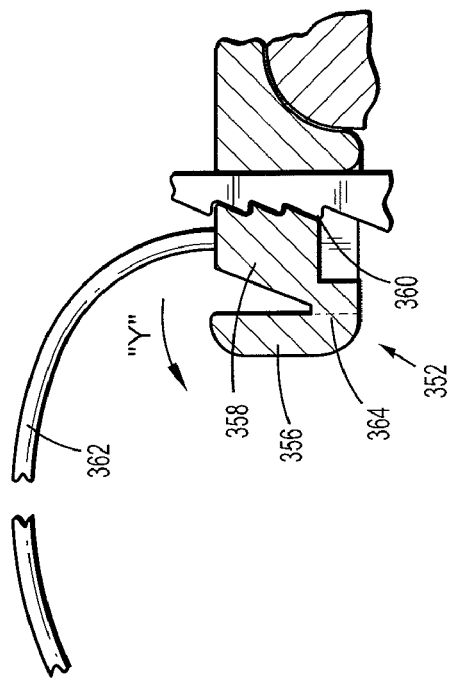

FIGS. 3A-3B illustrate an alternate embodiment of the present disclosure. In accordance with this embodiment, portal apparatus 300 includes portal member 302 having a plurality of longitudinal ports 304 for reception and passage of instrumentation in substantial fluid tight relation therewith and constricting element 306. Constricting element 306 may be attached, secured, or embedded within leading end 308 of portal member 302 by conventional means. Constricting element 306 may define an annular shape either circumscribing or extending around a peripheral segment of leading end 308 of portal member 302. Constricting element 306 further includes a lock 310 which secures the constricting element 306 in at least one defined annular or diametrical configuration. In one embodiment, constricting element may be secured via lock 310 to define a plurality of different sized annular loops. One suitable apparatus which may be adapted or modified for use with portal member 302 as a constricting element 306 and associated lock 310 is the serrated strap disclosed in commonly assigned U.S. Pat. No. 5,462,542 to Alesi, the entire contents of which are hereby incorporated in its entirety by reference herein. This serrated strap 350 is depicted in FIGS. 4A and 4B. Strap 350 includes buckle 352 and strap member 354 extending from the buckle 352. The buckle 352 includes base 356 and pawl 358 pivotally mounted and adapted to selectively engage pawl teeth 360 of strap member 354 as the strap member 354 is pulled through the buckle 352 while reducing the internal dimension of the loop created by the strap member 354. As one modification to strap 350, a release member 362 may be secured to pawl 358 of buckle 352 (see also FIG. 3C). Pawl 358 may be detachably connectable to base 356 within buckle 352 by, e.g., creating a zone or line of perforation 364 adjacent the location where the pawl 358 is connected to the base 356. Thus, application of a force via release member 362 will cause pawl 358 to become detached from base 356 thereby releasing strap member 354 and permitting leading end 308 to assume its normal expanded condition. In the alternative, release member 362 may be permanently secured to pawl 358 whereby the release member 362 will cause release of the pawl 358 (in direction "y") from pawl teeth 360 of strap member 354 without detachment of the pawl 358, while still releasing strap member 354 and permitting leading flange to assume its normal expanded condition.

Figure 5A:
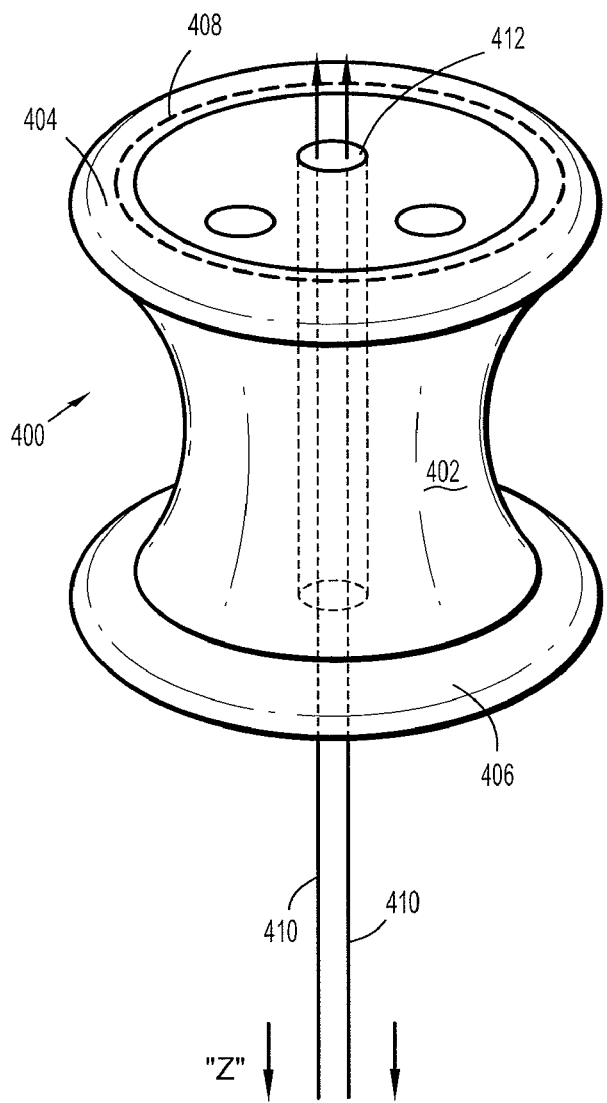
FIGS. 5A-5B are views of another embodiment of the surgical portal assembly illustrating the portal member in respective expanded and contracted conditions.
Figure 5B:
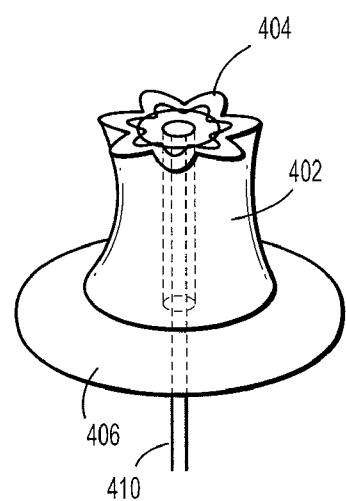

FIGS. 5A-5B illustrate another embodiment of the portal apparatus of the present disclosure. Portal apparatus 400 includes portal member 402 of similar design to the aforedescribed portal members. Portal member 402 may include leading and trailing flanges 404, 406 which may secure the portal member 402 on opposed sides of a cavity wall, e.g., the peritoneal cavity wall. Flanges 404, 406 may be separate or monolithically formed with portal member 402. Portal apparatus 400 further includes cinch member 408 attached, secured or otherwise embedded within leading flange 404 of portal member 402 around at least a portion of the leading flange 404. At least one, e.g., two leads 410, are connected to cinch member 408 with the free ends of the leads 410 extending through at least one longitudinal passageway 412 of portal member 402. Leads 410 may be pulled in a proximal direction "z" away from cinch member 408 to reduce the effective diameter of the cinch member 408 and cause contraction of the annular configuration or shape of leading flange 404. When in the contracted condition of FIG. 5B, leading flange 404 is first introduced within the tissue tract followed by insertion of the portal member 402. Once appropriately positioned relative to the tissue, e.g. abdominal wall, the free ends of leads 410 are released permitting leading flange 404 to expand to its normal condition of FIG. 5A. In this position, leading flange 404 may abut the internal surface of peritoneal cavity and outer flange 406 may abut the dermal tissue segments.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A surgical portal assembly, which comprises:
   a portal member adapted for positioning within a tissue tract, the portal member defining a longitudinal axis and having leading and trailing ends, the portal member including a first longitudinal port and a second longitudinal port for passage of an object, the portal member comprising a compressible material and being adapted to transition between a first expanded condition to facilitate securing of the portal within the tissue tract and in substantial sealed relation with tissue surfaces defining the tissue tract, and a second compressed condition to facilitate at least partial insertion of the portal within the tissue tract; and
   a first elongated member and a second elongated member extending through the respective first and second longitudinal ports and mechanically couplable to the portal member adjacent the leading end thereof, the first and second elongated members adapted to move through the respective first and second longitudinal ports in a trailing direction to exert a compressive force at least adjacent the leading end to cause the portal member to transition toward the compressed condition,
   wherein the leading end of the portal member defines a first cross-sectional dimension when in the first expanded condition, wherein the first and second elongated members are arranged to cause the leading end of the portal member to define a second cross-sectional dimension less than the first cross-sectional dimension when the first and second elongated members are moved through the respective first and second longitudinal ports in the trailing direction, wherein the first and second elongated members are arranged to extend through the respective first and second longitudinal ports of the portal member, around the leading end and along an outer surface of the portal member.

2. The surgical portal assembly according to claim 1 wherein the portal includes a third longitudinal port, the third longitudinal port having a third elongated member extending therethrough and being attachable to the portal member adjacent the leading end thereof, the third elongated member adapted to move through the third longitudinal port in the trailing direction to cause the portal member to transition toward the compressed condition.

3. The surgical portal assembly according to claim 1 wherein the first and second elongated members are adapted to attach to the outer surface of the portal member adjacent the leading end.

4. The surgical portal assembly according to claim 1 wherein the first and second elongated members are arranged to cause the leading end of the portal member to move toward the first cross-sectional dimension when outer segments of the elongated member extending along the outer surface of the portal member are advanced in a leading direction.

5. The surgical portal assembly according to claim 1 wherein the longitudinal ports of the portal member are dimensioned to extend between the leading and trailing ends and are adapted for reception of an object whereby compressible material defining the ports is adapted to deform to establish a substantial sealed relation with the object.

6. The surgical portal assembly according to claim 1 wherein the portal comprises one of a foam material or a gel material.

7. The surgical portal assembly according to claim 1 wherein the elongated member comprises a material selected from the group consisting of plastic, metal, and shape-memory alloy.

8. The surgical portal assembly according to claim 1, further comprising:

a biasing element disposed at the leading end of the portal member, wherein the biasing element restores the leading edge of the portal member to a first expanded condition and is adapted to move the elongated member through the at least one longitudinal port in a leading direction.

* * * * *